US007641663B2

(12) United States Patent
Hodorek

(10) Patent No.: US 7,641,663 B2
(45) Date of Patent: Jan. 5, 2010

(54) FEMORAL REFERENCE TIBIAL CUT GUIDE

(75) Inventor: Robert A. Hodorek, Warsaw, IN (US)

(73) Assignee: Zimmer Technology, Inc., Warsaw, IN (US)

(*) Notice: Subject to any disclaimer, the term of this patent is extended or adjusted under 35 U.S.C. 154(b) by 232 days.

(21) Appl. No.: 11/751,969

(22) Filed: May 22, 2007

(65) Prior Publication Data
US 2007/0219560 A1 Sep. 20, 2007

Related U.S. Application Data

(62) Division of application No. 10/370,049, filed on Feb. 20, 2003, now Pat. No. 7,235,080.

(51) Int. Cl.
A61B 17/58 (2006.01)
A61F 2/00 (2006.01)
(52) U.S. Cl. ...................................................... 606/88
(58) Field of Classification Search ............. 606/87–90, 606/105
See application file for complete search history.

(56) References Cited

U.S. PATENT DOCUMENTS

| 3,756,242 | A |   | 9/1973  | Co |
|-----------|---|---|---------|-----|
| 4,406,568 | A |   | 9/1983  | Rogers et al. |
| 4,487,203 | A | * | 12/1984 | Androphy ............... 606/88 |
| 4,524,766 | A |   | 6/1985  | Petersen |
| 4,566,448 | A |   | 1/1986  | Rohr, Jr. |
| 4,738,253 | A |   | 4/1988  | Buechel et al. |
| 4,759,350 | A |   | 7/1988  | Dunn et al. |
| 4,938,762 | A |   | 7/1990  | Wehrli |
| 5,217,463 | A | * | 6/1993  | Mikhail ................. 606/88 |
| 5,250,050 | A |   | 10/1993 | Poggie et al. |
| 5,676,668 | A |   | 10/1997 | McCue et al. |
| 5,800,438 | A |   | 9/1998  | Tuke et al. |
| 5,860,980 | A |   | 1/1999  | Axelson et al. |
| 6,296,646 | B1 |  | 10/2001 | Williamson |
| 6,344,043 | B1 |  | 2/2002  | Pappas |
| 6,478,799 | B1 |  | 11/2002 | Williamson |
| 6,648,896 | B2 |  | 11/2003 | Overes et al. |
| 6,758,850 | B2 |  | 7/2004  | Smith et al. |
| 6,770,077 | B2 |  | 8/2004  | Van Zile et al. |
| 2002/0133164 | A1 | | 9/2002 | Williamson |
| 2004/0087960 | A1 | | 5/2004 | Kinnett |
| 2004/0249387 | A1 | | 12/2004 | Faoro |

OTHER PUBLICATIONS

Zimmer Inc., Nexgen Complete Knee Solution: Revision Instrumentation Surgical Technique for Legacy Knee Constrained Condylar Knee, 2001, pp. 1, 7-10, 60.
Zimmer Inc., Nexgen Complete Knee Soution: Surgical Technique for Cruciate Retaining Knees and Revision Instrumentation Surgical Technique for Cruciate Retaining Augmentable Knees, 202, pp. 1, 70-78, 139.

* cited by examiner

Primary Examiner—Anu Ramana
(74) Attorney, Agent, or Firm—Baker & Daniels LLP

(57) ABSTRACT

A femoral reference tibial cut guide for cutting the proximal tibia to receive a tibial implant. The cut guide references the femur to determine the appropriate tibial resection.

20 Claims, 3 Drawing Sheets

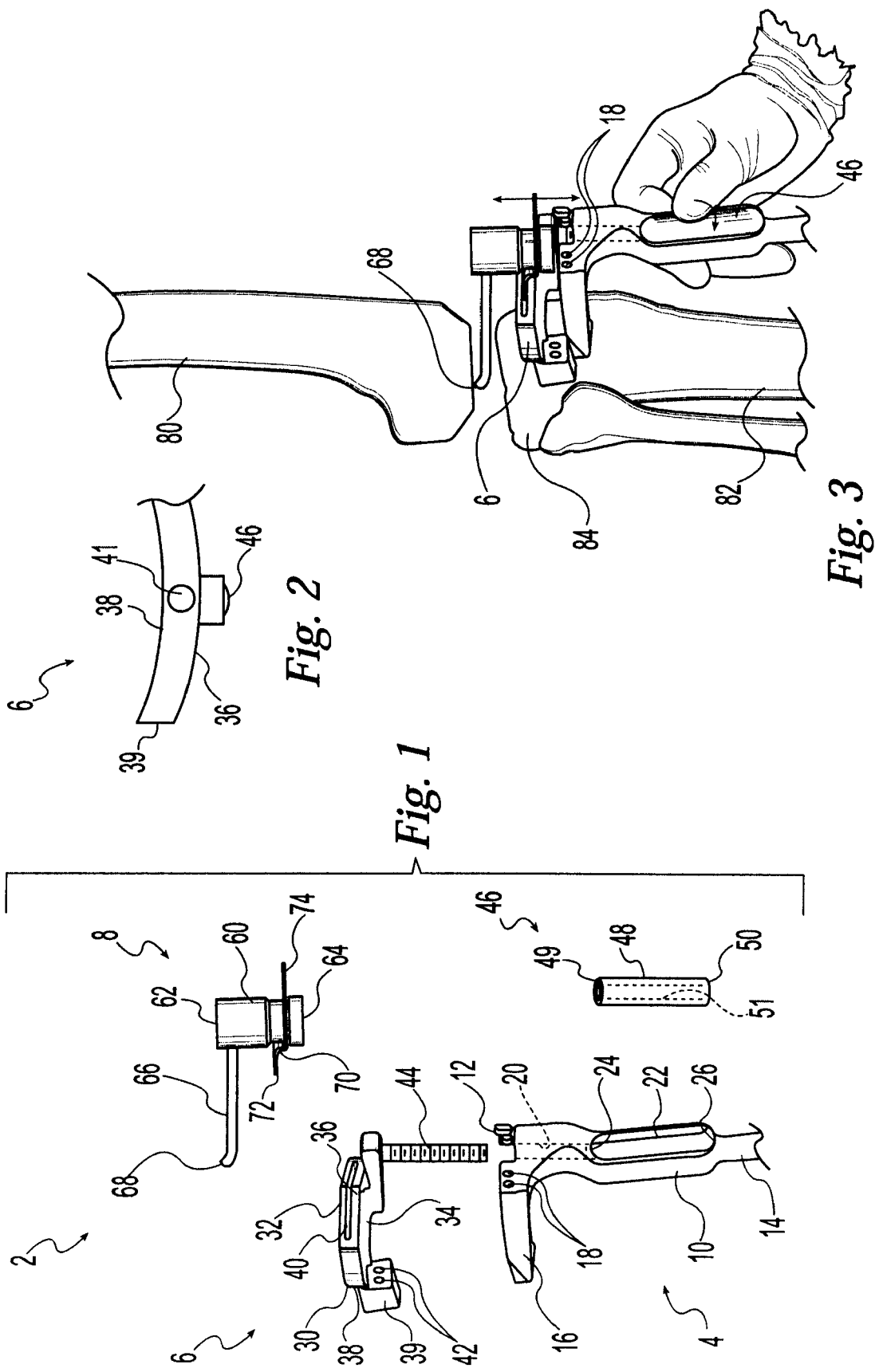

FEMORAL REFERENCE TIBIAL CUT GUIDE

CROSS-REFERENCE TO RELATED APPLICATIONS

This application is a divisional of U.S. patent application Ser. No. 10/370,049, entitled FEMORAL REFERENCE TIBIAL CUT GUIDE, filed on Feb. 20, 2003, assigned to the assignee of the present application, the disclosure of which is expressly incorporated herein by reference.

FIELD OF THE INVENTION

The present invention relates to a bone cutting guide, in particular to a guide for cutting the proximal tibia which establishes the tibial cut level by referencing the femur.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is an exploded oblique elevation view of an illustrative tibial cut guide assembly according to the present invention.

FIG. 2 is a top plan view of the tibial cut guide assembly of FIG. 1.

FIG. 3 is an oblique elevation view of the tibial cut guide assembly of FIG. 1 positioned adjacent a knee joint in extension.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 4:
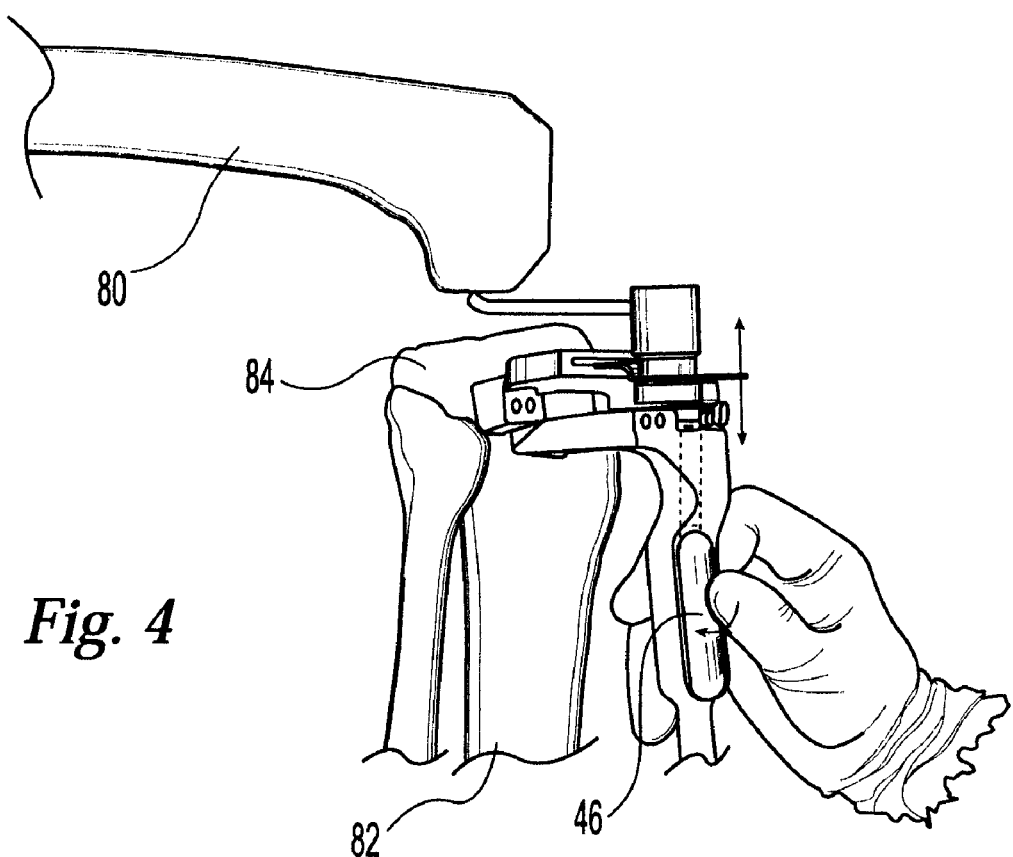
FIG. 4 is an oblique elevation view of the tibial cut guide assembly of FIG. 1 positioned adjacent a knee joint in flexion.

FIGS. 1-4 depict an illustrative tibial cut guide 2 assembly comprising a base 4, a cut head 6, and a depth reference probe 8. The base 4 includes an elongate body 10 having a proximal end 12, a distal end 14, and a longitudinal axis extending from the proximal end to the distal end. A pair of support arms 16 extends medially and laterally from the proximal end generally perpendicular to the longitudinal axis. Fixation holes 18 extend through the base 4 at the proximal end 12. A longitudinal bore 20 opens at the proximal end and extends along a portion of the longitudinal axis. A side opening 22 in the base 4 includes a top surface 24 and bottom surface 26. The longitudinal bore 20 extends through the top and bottom of the side opening 22 to communicate with the side opening 22.

The cut head 6 includes a body 30 having a proximal surface 32, a distal surface 34, an anterior side 36, a posterior side 38, a lateral side 39, and a medial side (not labeled) opposite the lateral side 39. A saw guide slot 40 extends through the cut head 6 from the anterior side 36 to the posterior side 38 to define a cutting plane having a downward posterior slope, typically on the order of 7°. The proximal surface 32 is parallel to the slot and can alternatively be used as a saw guiding surface offset a known distance from the slot. A mounting hole 41 extends from the proximal surface 32 down to communicate with the slot 40. Fixation holes 42 extend through the medial side and lateral side 39 of the cut head body 30 directed from anterior to posterior. A threaded, elongate elevation shaft 44 extends downwardly from the distal surface 34. An adjustment knob 46 includes an elongate cylindrical body 48 having a proximal end 49, a distal end 50, and a threaded through bore 51. The body 48 of the knob 46 is sized to fit within the side opening 22 with its through bore 51 aligned with the base through bore 20 and its proximal 49 and distal 50 ends adjacent the top 24 and bottom 26 surfaces of the side opening 22. The side of the knob 46 projects through the side opening 22 to provide access to turn the knob 46.

The cut head 6 is assembled to the base 4 by inserting the adjustment knob 46 into the side opening 22 and inserting the elevation shaft 44 into the longitudinal through bore 20. The adjustment knob is then threaded onto the elevation shaft 44 to retain the cut head 6 in the base 4. The cut head 6 is constrained against proximal-distal motion by the abutment of the proximal end 49 and distal end 50 of the knob 46 with the top 24 and bottom 26 of the side opening 22. Proximal-distal adjustment of the cut head is accomplished by turning the knob 46 which moves the elevation shaft 44 relative to the knob.

A depth reference probe 8 includes a cylindrical body 60 having a proximal end 62, a distal end 64, and a longitudinal axis extending from the proximal end 62 to the distal end 64. A probe arm 66 extends from the body 60 adjacent the proximal end 62 generally perpendicular to the body axis. The arm 66 terminates at an upturned probe tip 68. An engagement tab 70 extends from the body 60 adjacent the distal end 64 generally perpendicular to the body axis. The tab 70 is double ended, having a first end 72 spaced a first axial distance from the probe tip 68 and a second end 74 spaced a second axial distance from the probe tip 68 as measured along the longitudinal axis of the body 60. Each end is marked with the tibial implant thickness required to restore the knee to the spacing existing at the time the probe is used to position the tibial cut guide. The engagement tab 70 is mounted on the body 60 for rotation about the longitudinal axis so that the first and second ends 72, 74 can be alternately positioned on the same side of the body as the probe tip 68. The first and second ends 72, 74 of the engagement tab 70 are sized to fit within the saw guide slot 40.

FIG. 3 shows the cut guide assembly in process of being mounted adjacent a knee joint including a femur 80 and a tibia 82. The base 4 is positioned adjacent the proximal end 84 of the tibia 82 with the support arms 16 in contact with the tibia and the longitudinal base axis parallel to the tibial bone axis. Fixation pins are inserted through the base fixation holes 18 to anchor the base 4 in position. The knee is placed in zero degrees of flexion and the bones are distracted to the extent permitted by the soft tissues surrounding the joint. Distraction can be accomplished by using a retractor, by using traction, or by other suitable means. The adjustment knob 46 is turned to move the cut head and probe tip 68 up until the tip 68 contacts the distal femoral bone. This sets the tibial resection level to a known distance from the femoral bone.

Tibial implants are typically provided as one-piece or two-piece constructs. The probe 8 is sized to correspond to the available total tibial implant thicknesses so that when the tibia 82 is cut, the surgeon is assured that there is a tibial implant with a total thickness that will exactly replace the cut bone and reproduce the joint spacing and soft tissue tension that existed at the time the probe adjustment was made. When the probe 8 is to be used with a femur 80 that has already been cut to receive a femoral implant, as shown in FIG. 2, the probe spacing includes the thickness of the femoral implant as well as the thickness of the tibial implant. However, femoral implants are typically designed to replace the same amount of bone regardless of size, so only the tibial implant thickness needs to be shown on the probe 8. When the probe 8 is to be used with an uncut femur, the probe spacing corresponds to the thickness of the tibial implant. Each probe 8 can have two spacings that are alternatively selectable as shown in the illustrative embodiment and multiple probes can be provided that correspond to a variety of possible implant thicknesses.

After the desired resection level is set, fixation pins are inserted through the cut head fixation holes 42 to fix the cut head 6 in position. The probe 8 is removed and a saw blade is activated through the saw slot 40 to cut the proximal tibia 84 at the desired level. The cut head 6 and base 4 are then removed and the implants inserted.

In addition to setting the resection level with the knee in zero degrees of flexion, the tibial cut guide assembly can be used at other flexion positions between zero degrees and full flexion. FIG. 4 shows the illustrative cut guide assembly 2 mounted on the knee in approximately ninety degrees of flexion. The resection level is set as described above. Furthermore, after the resection level is set at one angle of knee flexion, the knee can be repositioned and compared to the cut guide assembly to see if the same resection level will suffice for the new position. If not, the soft tissues constraining the knee joint can be selectively cut to balance the resection level at different flexion angles. The resection level can also be adjusted to a compromise position.

Figure 5:
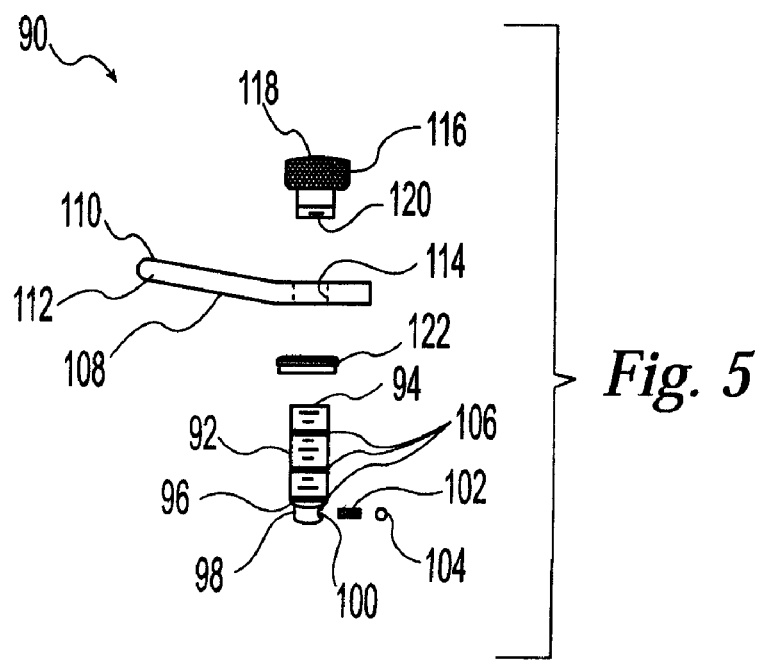
FIG. 5 is an exploded side elevation view of an alternative illustrative embodiment of a depth reference probe.
Figure 6:
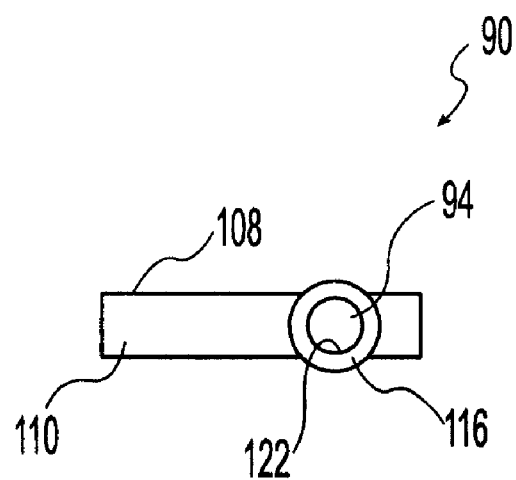
FIG. 6 is a top plan view of the alternative depth reference probe of FIG. 5.
Figure 7:
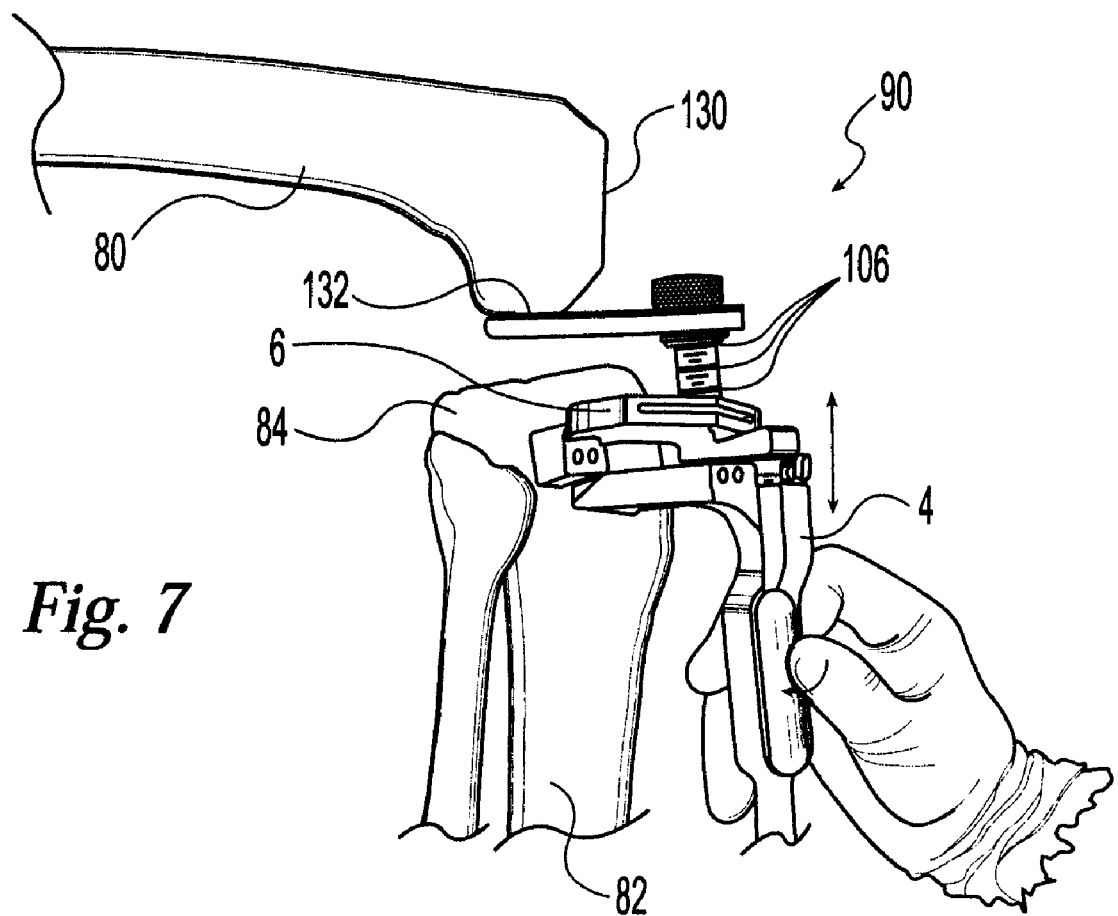
FIG. 7 is an oblique elevation view of the alternative depth reference probe mounted on the cut guide of FIG. 1 and positioned adjacent a knee joint in flexion.

FIGS. 5-7 show an alternative illustrative embodiment of a probe 90. The probe 90 includes a threaded, elongate shaft 92 having a proximal end 94, a distal end 96, and a longitudinal axis from the proximal end 94 to the distal end 96. A cut guide engaging portion 98 is formed adjacent the distal end 96 and includes a bore 100 containing a spring 102 and a ball 104. Size indicia or marks 106 corresponding to the available total tibial implant thicknesses are spaced along the shaft. A probe blade 108 includes a flat upper surface 110, a lower surface 112, and a through hole 114 from the upper surface to the lower surface. A knob 116 comprises a cylindrical body having a proximal end 118, a distal end 120, and a longitudinal axis from the proximal end 118 to the distal end 120. A threaded, axial through bore extends through the knob 116 from the proximal end 118 to the distal end 120. The exterior of the knob 116 is threaded adjacent the distal end 120. The externally threaded portion of the knob fits through the hole 114 in the blade and is held in place by a nut 122 threaded onto the distal end of the knob 116. After tightening the nut 122, the knob 116 remains rotatable relative to the blade 108. The knob 116 is threadably received on the shaft 92 such that by turning the knob relative to the shaft 92 and blade 108, the blade 108 can be positioned up and down on the shaft. The implant thickness setting is read by noting which mark 106 is adjacent the nut 122.

In use, the probe 90 is mounted on the cut head 6 by inserting the cut guide engaging portion 98 into the mounting hole 41 until the ball 104 snaps into the slot 40 to retain the probe in place. The longitudinal axis of the probe shaft 92 will be perpendicular to the proximal surface 32 of the cut head and thus perpendicular to the slot 40 of the illustrative embodiment. The blade is angled to compensate for the posterior slope of the slot 40 and proximal surface 32 of the cut head 6 such that the upper surface 110 of the blade 108 is approximately horizontal when the tibia 82 is oriented vertically. The blade 108 is adjusted to a desired implant thickness setting by turning the probe knob 116 until the nut 122 is adjacent the desired mark 106.

With the base 4 of the cut guide assembly pinned to the tibia 82, the cut head 6 is adjusted up and down by turning the adjustment knob 46 until the blade 108 contacts the femur. If it is desirable to remove more or less bone from the tibia 82, the knob 116 is turned to adjust the blade up or down the shaft to the next mark 106 corresponding to a tibial implant thickness and then the cut head 6 is repositioned. The knee can be positioned in different degrees of flexion, such as zero and ninety degrees, to set the tibial cut depth. The adjustability of the blade 108 of this embodiment also makes it possible to get a direct reading in millimeters comparing the gap between the femur and tibia at different flexion angles. For example, the guide can first be set with the knee in full extension. After repositioning the knee to ninety degrees of flexion, the knob 116 can be turned to reposition the blade 108 against the bone. The difference in the flexion and extension gaps is shown by the difference between the marks 106 on the probe shaft 92 that aligned with the blade in the two knee positions.

Where the femoral bone has already been cut, as shown in the FIG. 7, the flat upper surface 110 of the blade facilitates positioning the femur 80 at flexion angles corresponding to the femoral bone cuts. For example, in extension, the distal cut surface 130 will lie flat against the blade 108. In flexion, the posterior cut surface 132 will lie flat against the blade. The blade 108, can be narrow, as shown, to contact one femoral condyle or corresponding cut surface at a time. Alternatively, the blade can be wide so that both condyles contact the blade at the same time. Likewise, the cut guide described above can be used with a unicondylar knee arthroplasty as well as a total knee arthroplasty.

It will be understood by those skilled in the art that the foregoing has described illustrative embodiments of the present invention and that variations may be made to these embodiments without departing from the spirit and scope of the invention defined by the appended claims. For example the illustrative embodiments depict using saw guides and blades to make the bone cuts. However, the claimed methods and cut guides could also be used with other bone removal systems to set their reference bases to achieve the desired position of the tibial resection.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of resecting the proximal end of a tibia, comprising the steps of:
   positioning a knee joint comprising a tibia and a femur in a desired alignment and spacing, the tibia and the femur defining a gap formed therebetween;
   positioning a tibial cutting guide adjacent to the proximal end of the tibia, the tibial cutting guide including a probe;
   inserting the probe in the gap;

contacting the femur with the probe to space the tibial cutting guide a known distance from the point at which the probe contacts the femur; and guiding a cutter with the tibial cutting guide to cut the tibia.

2. The method of claim 1, further comprising the step of removing the probe from the tibial cutting guide before cutting the tibia.

3. The method of claim 2, further comprising the step of anchoring the tibial cutting guide to the tibia before removing the probe.

4. The method of claim 1, wherein the probe spaces the tibial cutting guide from the femur a distance correlated to the available implant thicknesses, the method further comprising the steps of:

removing the tibial cutting guide after cutting the tibia; and replacing the cut bone with a tibial implant having a thickness correlated with the probe spacing.

5. The method of claim 1, further comprising the steps of:

selecting the probe from a plurality of probes corresponding to different available implant thicknesses; and connecting the selected probe to the tibial cutting guide before contacting the femur with the probe.

6. The method of claim 1, wherein the probe includes a reference surface and the probe is adjustable to position the reference surface at different known distances from the tibial cutting guide, the step of contacting the femur with the probe further comprising contacting the femur with the reference surface.

7. The method of claim 6, wherein the reference surface is a planar surface, the method further comprising the step of adjusting the flexion angle of the knee so that the cut surface of the femur is parallel with and in contact with the planar surface.

8. The method of claim 1, wherein the probe includes indicia corresponding to different available implant thicknesses and the probe is adjustable to position the reference surface relative to the indicia.

9. The method of claim 1, further comprising the step of cutting the femur to receive a femoral implant, the step of contacting the femur with the probe further comprising contacting the cut surface of the femur with the probe.

10. The method of claim 1, wherein the step of positioning the knee joint in a desired alignment and spacing further comprises separating the femur and tibia with a retractor.

11. The method of claim 1, wherein the step of positioning the knee joint in a desired alignment and spacing further comprises separating the femur and tibia using traction.

12. A method of determining the difference in spacing between the tibia and femur, comprising the steps of:

positioning a knee joint comprising a tibia and a femur at a first angle of flexion;

positioning a tibial cutting guide adjacent to the proximal end of the tibia, the tibial cutting guide including a probe, the probe including a reference surface for contacting the femur and a plurality of indicia indicating a linear distance from the reference surface to the tibial cutting guide, the reference surface being adjustable between the plurality of indicia;

contacting the femur with the reference surface in a first position;

fixing the position of the tibial cutting guide;

determining the first index corresponding to the reference surface first position;

repositioning the knee joint to a second angle of flexion;

contacting the femur with the reference surface in a second position;

determining the second index corresponding to the reference surface second position; and comparing the first index to the second index to determine the difference in the spacing between the femur and tibia in the two flexion positions.

13. The method of claim 12, wherein the two flexion angles are approximately 0° degrees of flexion and approximately 90° of flexion.

14. A method of resecting a proximal end of a tibia, comprising the steps of:

positioning a tibia and a femur to create a gap therebetween;

providing a cutting guide having a cutting slot formed therein;

connecting a moveable probe to the cutting guide;

spacing the probe a fixed distance from the cutting slot;

inserting the probe into the gap;

advancing the cutting guide until the probe contacts the femur; and resecting the proximal end of the tibia through the cutting slot.

15. The method of claim 14, further comprising the step of removing the probe from the cutting guide before resecting the proximal end of the tibia.

16. The method of claim 15, further comprising the step of anchoring the cutting guide to the tibia before removing the probe.

17. The method of claim 14, further comprising the step of selecting the moveable probe from a plurality of probes corresponding to different available implant thicknesses.

18. The method of claim 14, further comprising, prior to the inserting step, the step of resecting the distal femur, the advancing step further comprising advancing the cutting guide until the probe contacts the resected femur.

19. The method of claim 14, wherein the positioning step further comprises positioning the tibia and the femur at approximately 0° degrees of flexion.

20. The method of claim 14, wherein the positioning step further comprises positioning the tibia and the femur at approximately 90° of flexion.

* * * * *